(12) United States Patent
Tretjak et al.

(10) Patent No.: US 11,926,588 B2
(45) Date of Patent: *Mar. 12, 2024

(54) METHOD FOR PURIFYING (METH)ACRYLIC ESTERS USING A DIVIDED WALL COLUMN

(71) Applicant: Arkema France, Colombes (FR)

(72) Inventors: Serge Tretjak, Saint Avold (FR); Yves Cabon, Saint Avold (FR); Andre Levray, Saint Avold (FR); Camille Hilpert, Saint Avold (FR); Anne Moreliere, Saint Avold (FR)

(73) Assignee: Arkema France, Colombes (FR)

( * ) Notice: Subject to any disclaimer, the term of this patent is extended or adjusted under 35 U.S.C. 154(b) by 265 days.

This patent is subject to a terminal disclaimer.

(21) Appl. No.: 17/424,204

(22) PCT Filed: Jan. 21, 2020

(86) PCT No.: PCT/FR2020/050075
§ 371 (c)(1),
(2) Date: Jul. 20, 2021

(87) PCT Pub. No.: WO2020/152415
PCT Pub. Date: Jul. 30, 2020

(65) Prior Publication Data
US 2022/0106251 A1    Apr. 7, 2022

(30) Foreign Application Priority Data

Jan. 22, 2019 (FR) .................................. 19.00541

(51) Int. Cl.
C07C 67/08    (2006.01)
C07C 67/54    (2006.01)

(52) U.S. Cl.
CPC .............. *C07C 67/08* (2013.01); *C07C 67/54* (2013.01)

(58) Field of Classification Search
CPC ......... B63B 21/50; C07C 67/08; C07C 67/54; C07C 69/54; F03B 11/00; F03B 13/20; F05B 2220/706; H01B 7/14; H02G 7/00; H02G 9/12; Y02E 10/30; B01L 1/52; B01L 2300/105; B01L 9/06; C12Q 1/46; C12Y 301/01007; G01N 2430/00; G01N 33/52
See application file for complete search history.

(56) References Cited

U.S. PATENT DOCUMENTS

| | | | |
|---|---|---|---|
| 5,510,514 A | 4/1996 | Fauconet et al. | |
| 6,320,070 B1 | 11/2001 | Aichinger | |
| 6,956,130 B2 | 10/2005 | Riondel et al. | |
| 8,894,821 B2 | 11/2014 | Lee et al. | |
| 2007/0129571 A1* | 6/2007 | Yada | B01D 3/322 562/545 |
| 2018/0065061 A1* | 3/2018 | Hoyme | C07C 45/80 |
| 2020/0094160 A1* | 3/2020 | Lang | B01D 3/225 |

FOREIGN PATENT DOCUMENTS

| | | | |
|---|---|---|---|
| EP | 1247795 A1 * | 10/2002 | ............. C07C 67/08 |
| JP | 2005239564 A2 | 9/2005 | |

OTHER PUBLICATIONS

US 8,858,761 B2, 10/2014, Lee et al. (withdrawn)
JP2005 239564 translation, 17 pages (Year: 2005).*
EP1247795 translated 5 pages (Year: 2002).*
Dejanovic I et al. "Dividing wall column—A breakthrough towards sustainable distilling", Chemical Engineering and Processing, Elsevier Sequoia, Lausanne, vol. 49, No. 6, Jun. 1, 2010, pp. 559-580, CH. ISSN: 0255-2701, XP027138843 (p. 562, figure 5a).
Asprion N. et al. "Dividing wall columns: Fundamentals and recent advances", Chemical Engineering and Processing, Elsevier Sequoia, Lausanne, vol. 49, No. 2, Feb. 1, 2010, pp. 139-146, ISSN:0255-2701. XP02693878, p. 141, figure 3b, p. 143, figure 8.

* cited by examiner

Primary Examiner — Jafar F Parsa
Assistant Examiner — Blaine G Doletski
(74) Attorney, Agent, or Firm — Lynn B. Morreale

(57) ABSTRACT

The invention relates to the production of (meth)acrylic esters according to a process by direct esterification, and in particular to the purification of a crude reaction mixture comprising a $C_4$-$C_{12}$ (meth)acrylic ester using a dividing wall column employed in a particular configuration. The dividing wall column is equipped with a separating wall creating separation zones in the column, the wall not being joined to the upper dome of the column in the top part and being joined to the bottom of the column in the bottom part. The process according to the invention guarantees a product of very high purity, independently of the back-cracking reactions of the heavy by-products liable to arise during the purification of the product sought.

13 Claims, 1 Drawing Sheet

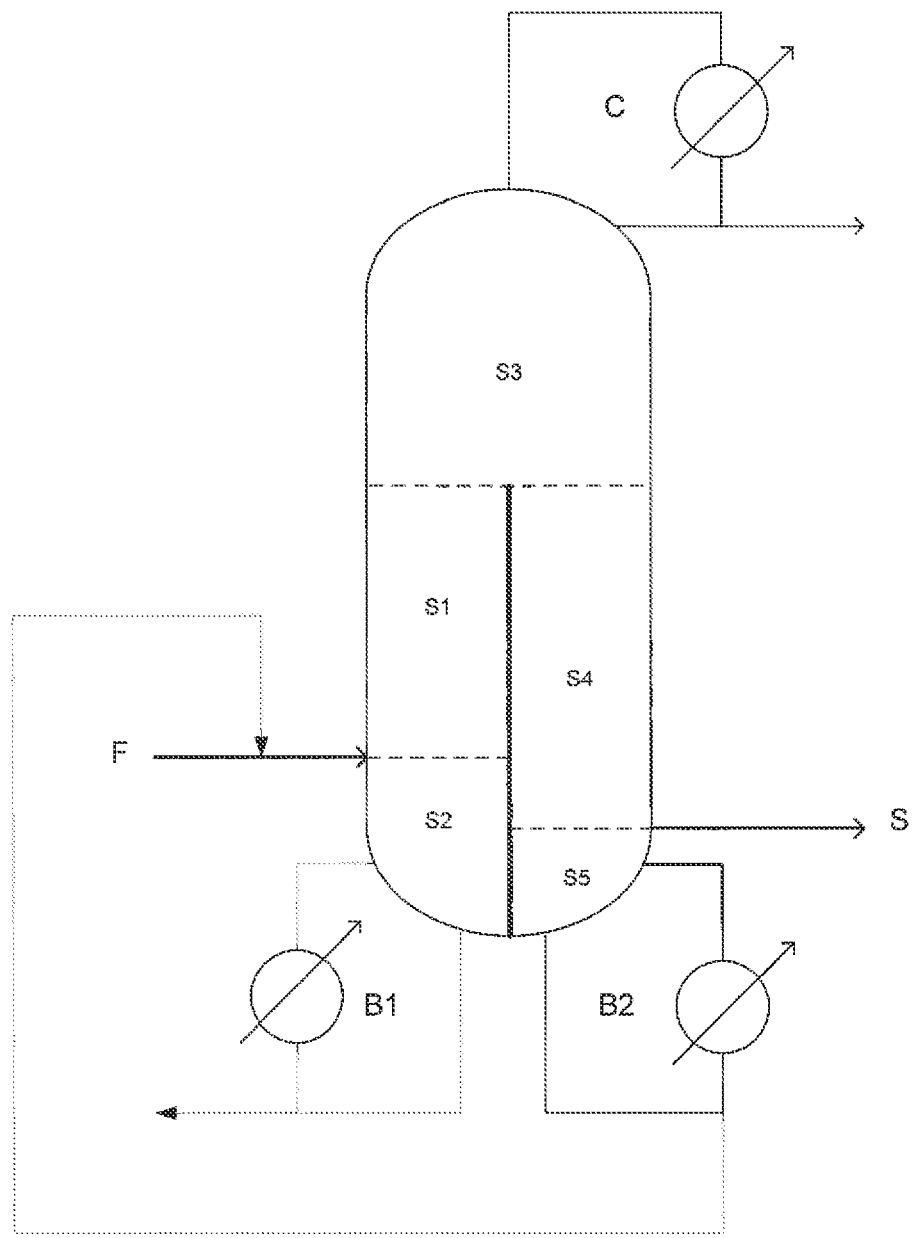

METHOD FOR PURIFYING (METH)ACRYLIC ESTERS USING A DIVIDED WALL COLUMN

CROSS-REFERENCE TO RELATED APPLICATIONS

This application is a national stage application under 35 U.S.C. § 371 of PCT/FR2020/050075, filed Jan. 21, 2020 which claims benefit to application FR19.00541, filed Jan. 22, 2019.

TECHNICAL FIELD

The present invention relates to the production of (meth) acrylic esters according to a process by direct esterification and in particular to the purification of a crude reaction mixture comprising a $C_4$-$C_{12}$ (meth)acrylic ester using a dividing wall column employed in a particular configuration.

This configuration leads to a simplification of the purification process and guarantees a product of very high purity, independently of the back-cracking reactions of the heavy by-products liable to arise during the purification of the product sought.

The invention also relates to a process for producing a $C_4$-$C_{12}$ (meth)acrylic ester comprising this recovery/purification process.

Technical, Background and Technical Problem $C_4$-$C_2$ (meth)acrylic esters can be synthesized by direct esterification reaction of the (meth)acrylic acid with the corresponding $C_4$-$C_{12}$ alcohol. This reaction is generally carried out in the presence of a homogeneous catalyst, in particular an acid catalyst, such as sulfuric acid or para-toluenesulfonic acid.

Esterification is an equilibrated reaction with generation of water, where the removal of the water in order to shift the equilibrium towards the production of the (meth)acrylic ester can be effected in the form of an azeotrope using an excess of the esterifying alcohol.

Side reactions during the synthesis produce impurities, generally by-products with a high boiling point or one close to the boiling point of the ester sought, generally in the form of compounds referred to as Michael adducts. These compounds have to be removed in order to obtain the (meth) acrylic ester with a high purity meeting the technical requirements associated with its end use.

For these purposes, a separation/purification process is generally carried out, comprising a series of distillations, extractions and/or decantations, which are expensive operations from the viewpoint of energy, yield and of course in terms of investment and construction cost for an industrial plant.

The purification operations are complex to implement, in particular due to the presence of azeotropic mixtures, but also because of the presence of a, generally acid, homogeneous catalyst in the reaction medium to be purified. In the case for example of catalysis with sulfuric acid, the esterification reaction generates a reaction mixture comprising the ester sought, the residual reactants alcohol and acid and the sulfuric acid in the form of alkyl hydrogen sulfate. The reaction mixture is then subjected to a neutralization, for example by addition of an aqueous solution of a base, followed by treatment of the aqueous phase and of the organic phase which are separated after decantation, as described for example in the documents EP 609 127 and EP 1 247 793. However, in the event of incomplete neutralization or incomplete washing of the separated organic phase, the residual acidity can cause problems of degradation of the acrylic ester formed or the cracking of the Michael adducts during steps of purification of the organic phase. Under these conditions, a high purity for the (meth)acrylic ester becomes difficult to achieve.

U.S. Pat. No. 6,320,070 describes operating conditions of the synthesis of (meth)acrylic esters by direct esterification catalyzed by sulfuric acid, minimizing the formation of Michael adducts and including the extraction of an aqueous phase concentrated in catalyst which is reintroduced to the reaction. However, this document does not mention the problems linked to the possible presence of residual acidity in the mixture subjected to the purification steps.

In general, the prior art documents combine, in the processes of direct esterification in the presence of a homogeneous catalyst such as sulfuric acid, a separation and a prior neutralization with a base such as caustic soda, a decantation followed by a washing of the organic phase before purification using a topping column (distillation of the light compounds) and a tailing column (separation of the heavy compounds). In all cases, the purification thus carried out does not make it possible to obtain a final product of high purity under economical conditions and with a high recovery rate.

With the development of dividing wall distillation columns (known under the acronym DWC—dividing wall column), simplified purification processes are now being proposed. This technology is based on a distillation column comprising an internal separating wall which makes it possible to combine the operation of two columns conventionally in series in a single item of equipment, by employing a reboiler and a single condenser.

By way of example, the patent application EP 2 659 943 describes a configuration of a dividing wall column and its operation in a process for the production of 2-ethylhexyl acrylate of high purity. Although this column is complex to manufacture and to operate, it exhibits the advantage of reducing the equipment cost and the energy consumption of the purification process, in comparison with a conventional plant comprising two distillation columns. The purification process described in this document makes no mention of problems related to the prior separation of the catalyst, the residual presence of which can cause retrogradation reactions in the dividing wall column. In addition, the question of the stabilization necessary for its satisfactory operation is not broached.

The patent application JP 2005-239564 also describes the use of a dividing wall column in a process for the synthesis of (meth)acrylic esters, exemplified in the case of the synthesis of butyl methacrylate by transesterification reaction between methyl methacrylate and butanol, in this process, a mist eliminator is associated with the dividing wall column in order to prevent the entrainment of droplets of stabilizers in the sidestream withdrawal and to control the amount of stabilizers in the purified product. The dividing wall column makes it possible to carry out the separation of the targeted ester with the heavy products and the lighter products. The purification process described in this document is applicable to the production of $C_1$-$C_4$ alkyl (meth) acrylates by direct esterification. However, it does not resolve the issue of the prior separation of the catalyst when the esters are sensitive to retrogradation reactions, in particular when the presence of the catalyst in the dividing wall column risks causing cracking reactions that lead to the formation of compounds which contaminate the purified product withdrawn as a sidestream.

In the document WO 2018/114429, a dividing wall column comprising a common lower portion connected to a single reboiler is used to purify 2-ethylhexyl acrylate or 2-propylheptyl acrylate. Here, too, this type of configuration does not pose the problem of back-cracking reactions liable to arise in the boiler of this column and generating light impurities such as the esterifying alcohol and, consequently, affecting the purity of the final product.

The technology of dividing wall columns in general is known and described, for example, by Asprion N. et al., "Dividing wall columns: Fundamentals and recent advances", Chemical Engineering and Processing, vol. 49 (2010), pages 139-146, or by Dejanovic I. et al., "Dividing wall column—A breakthrough towards sustainable distilling". Chemical Engineering and Processing, vol. 49 (2010), pages 559-580.

However, the different configurations described concern only the expected energy gain, and the prior art as a whole not once suggests the type of configuration suited to the purification of crude (meth)acrylic reaction mixtures resulting from a homogeneously catalyzed esterification reaction, in particular when the medium to be purified includes Michael adducts and an acid catalyst such as sulfuric acid.

There still remains a need to improve the purification of $C_4$-$C_{12}$ (meth)acrylic esters, such as for example 2-ethylhexyl acrylate or 2-octyl acrylate, so as to obtain a product of very high purity, independently of the back-cracking reactions of the heavy by-products which inevitably arise during the purification process.

The objective of the present invention meets this need by providing a process for recovering a $C_4$-$C_{12}$ (meth)acrylic ester purified using a purification system comprising a dividing wall column employed in a particular configuration, which makes it possible to avoid the risk of contamination of the finished ester produced by the retrogradation reactions in the presence of residual catalyst in the column.

The present invention thus provides a simplified process for recovering a $C_4$-$C_{12}$ (meth)acrylic ester of high purity, starting from a crude reaction mixture resulting from the direct esterification reaction of the (meth)acrylic acid with the corresponding alcohol, while at the same time optimizing the investment cost and the energy to be used in the plant.

SUMMARY OF THE INVENTION

One subject of the invention is a process for recovering a purified. $C_4$-$C_{12}$ (meth)acrylic ester, starting from a crude reaction mixture obtained by direct esterification of the (meth)acrylic acid with the corresponding $C_4$-$C_{12}$ alcohol, said process being characterized in that it is carried out using a purification system so comprising a dividing wall column equipped with a separating wall which is not joined to the upper dome of the column in the top part and is joined to the bottom of the column in the bottom part, and associated at the top with a single condenser and at the bottom with two boilers, said dividing wall column comprising a common rectification section above the wall, a prefractionation section comprising the feed of the column, and a withdrawal section separated from the prefractionation section by the wall and comprising the withdrawal of the purified ester.

According to one embodiment, a gas stream is extracted at the top of the rectification section, and recycled after condensation at least in part into the esterification reactor.

According to one embodiment, a stream is withdrawn at the bottom of the prefractionation section and recycled at least in part into the esterification reactor.

According to one embodiment, a stream is withdrawn at the bottom of the withdrawal section and recycled at least in part into the prefractionation section of the dividing wall column.

According to one embodiment, a stream of purified (meth)acrylic ester is withdrawn as a sidestream from the withdrawal section at a point situated above; the bottom withdrawal of said withdrawal section.

According to one embodiment, the direct esterification reaction is performed in the presence of a homogeneous catalyst, in particular an acid catalyst, such as sulfuric acid or para-toluenesulfonic acid.

According to one embodiment, the crude reaction mixture is subjected beforehand to neutralization with a base followed by decantation and washing of the organic phase before purification.

According to one embodiment, the crude reaction mixture subjected to the process for recovering the purified (meth)acrylic ester comprises at least in part the catalyst employed for the esterification reaction.

According to one embodiment, the purification system is stabilized using a single polymerization inhibitor, preferably injected at the top condenser, the purified (meth)acrylic ester being withdrawn as a sidestream from the dividing wall column in the form of an already stabilized liquid or gas stream.

According to one embodiment, the purification system is stabilized using a first polymerization inhibitor, preferably injected at the top condenser, the purified (meth)acrylic ester being withdrawn as a sidestream from the dividing wall column in the form of a gas stream which, after condensation, is subsequently stabilized with a polymerization inhibitor that is different from the first inhibitor.

According to the invention, the polymerization inhibitor used to stabilize the ester sought can be introduced into the purification system as single polymerization inhibitor; this results in the stabilization being simpler and consistent. Alternatively, a less expensive polymerization inhibitor can be used to stabilize the dividing wall column, and the purified ester is subsequently stabilized with another compound more suitable for stabilizing the finished product for the purpose of its subsequent storage and use. In this case, the cost related to the polymerization inhibitors can be greatly reduced.

According to the invention, the esterifying alcohol is a primary or secondary aliphatic alcohol, baying a linear or branched alkyl chain comprising from 4 to 12 carbon atoms, preferably from 5 to 10 carbon atoms.

Mention may be made, as examples of alcohol, of 2-ethylhexanol, 2-octanol or 2-propylheptanol. Preferably, the alcohol is 2-ethylhexanol.

The term "(meth)acrylic" means acrylic or methacrylic; the term "(meth)acrylate" means acrylate air methacrylate.

The (meth)acrylic acid is preferably acrylic acid.

According to a preferred embodiment, the purified $C_4$-$C_{12}$ (meth)acrylic ester is a purified acrylate, more preferentially 2-ethylhexyl acrylate or 2-octyl acrylate.

The recovery process according to the invention results in a $C_4$-$C_{12}$ (meth)acrylate with a purity superior to that obtained in a conventional plant comprising at least two separation columns, this being the case under more economical energy conditions, by virtue of operating conditions of the dividing wall column which minimize the thermal degradation of the heat-sensitive compounds present in the medium to be purified.

Another subject of the invention is the use of a purification system for recovering a purified $C_4$-$C_{12}$ (meth)acrylic ester, starting from a crude reaction mixture obtained by direct esterification of the (meth)acrylic acid with the corresponding $C_4$-$C_{12}$ alcohol, said purification system comprising a dividing wall column equipped with a separating wall which is not joined to the upper dome of the column in the top part and is joined to the bottom of the column in the bottom part, and associated at the top with a single condenser and at the bottom with two boilers, said dividing wall column comprising a common rectification section above the wall, a prefractionation section comprising the feed of the column, and a withdrawal section separated from the prefractionation section by the wall and comprising the withdrawal of the purified ester.

Another subject of the invention is a process for producing a $C_4$-$C_{12}$ (meth)acrylic ester of high purity by direct esterification of the (meth)acrylic acid with the corresponding $C_4$-$C_{12}$ alcohol, characterized in that the crude reaction mixture is subjected to the recovery process using the purification system as defined above.

Thus, the invention makes it possible to achieve the desired specifications in terms of purity of the (meth)acrylic esters under economical conditions, that is to say a purity of greater than 99.6%, indeed even greater than 99.8%.

BRIEF DESCRIPTION OF THE FIGURE

The single FIGURE represents the configuration of a purification system comprising a dividing wall column which can be used in the process according to the invention.

DETAILED ACCOUNT OF THE INVENTION

The invention is now described in greater detail and in a nonlimiting manner in the description that follows.

With reference to the FIGURE, the dividing wall column used in the process according to the invention comprises a partial vertical wall (or dividing wall) P placed inside the column, thus defining three distinct zones: an upper zone, denoted rectification section, a central zone comprising two zones on either side of the dividing wall and extending as far as the bottom of the column.

According to one embodiment, the wall can be in part diagonal. The wall can be flat or cylindrical, so that the spaces separated by the wall can be positioned in concentric form.

The wall as installed does not necessarily separate the central zone into two equal zones; this is because it can be advantageous in some embodiments to have unequal zones in order to minimize the loss of head or the tendency to choking, according to the nature or the intensity of the streams circulating in the column.

The height of the wall can represent from 30% to 70% of the height of the column.

The central zone consists of two zones on either side of the wall, one of which represents a "prefractionation" section and the other a withdrawal section for the pure product.

For the sake of simplicity in the continuation of the account of the invention, "prefractionation section" is understood to mean the section of the separating wall column which is fed by the stream of (meth)acrylic ester to be purified, the feeding only taking place on a single side of the wall, and "withdrawal section" is understood to mean the section of the column on the other side of the separating wall, from where the stream of purified (meth)acrylic ester is extracted as a sidestream.

The prefractionation section, associated with a boiler B1, comprises the feed F of the column, thus separating a section S1 above the feed and a section S2 below the feed. The prefractionation section has the effect of concentrating the most volatile products, known as light compounds, at the top of the column and of concentrating the least volatile is products, known as heavy compounds, at the bottom of the column. It is in particular in this prefractionation section, associated with the boiler B1, that a large part of the polymerization inhibitors and also the heavy impurities are found at the bottom of this section. This prefractionation bottom product can be reused by recycling all or part thereof into the esterification reactor, optionally after passage through a film evaporator.

According to one embodiment, the feed is located in the lower half of the prefractionation section, comprising S1+S2, preferably in the lower third, for example at plate 4.

The withdrawal section comprises a side outlet in order to withdraw the purified ester S, the side outlet dividing the withdrawal section into two sections S4 and S5. The withdrawal of the purified ester can be carried out in the form of a liquid stream or of a gas stream; preferably, a gas stream is withdrawn. In this section, the light compounds and also the ester are sent to the top of the column and heavy compounds are sent to the bottom of the column. A bottom stream essentially comprising heavy compounds and polymerization inhibitors and a small amount of ester produced is withdrawn from the withdrawal section associated with a boiler B2 and is advantageously recycled, at least in part, into the prefractionation section, preferably at the feed F, or at a point located above or below the feed. The optional recycling of the bottom product from the withdrawal section makes it possible to minimize the losses of (meth)acrylic ester.

According to one embodiment, the side-stream withdrawal point is located in the lower half of the withdrawal section, preferably in the lower quarter.

A common zone, known as rectification section S3, is found above the wall at the top of the dividing wall column, which section makes it possible to separate the light compounds, which are extracted, then condensed, at least in part, in the condenser C associated with the column. This condensed product is returned, in part, as reflux to the Section S3, the other part advantageously being sent, at least in part, to the inlet of the reactor, since it consists mainly of unreacted reactants and a small amount of ester formed.

The liquid reflux (not shown) on the prefractionation and withdrawal sections is provided by a collecting means allowing controlled distribution of the liquid from the bottom of the rectification section to the prefractionation and withdrawal sections, The mass fraction of liquid returning toward the section S1 is generally between 20% and 50%.

The bottom product of the withdrawal section likewise comprising a boiler B2 is advantageously recycled to the feed of the dividing wall column, thus making it possible to recycle and minimize the ester losses at the bottom of this withdrawal section.

A certain number of parameters characterize the design and the operation of the dividing wall column. They mainly concern the number of theoretical stages in each section of the dividing wall column, in particular the numbers N1, N2, N3, N4 and N5 corresponding respectively to the number of stages of each of the sections S1 to S5 described above, the reflux ratio of the column, the ratio of liquid stream originating from the rectification section on each side of the wall, the ratio of gas stream originating from the reboiling section on each side of the dividing wall, the positioning of the feed point F or of the point for sidestream withdrawal S of the pure product.

These different parameters can be determined from methods known to a person skilled in the art, so that the (meth)acrylic ester is produced with a purity meeting the desired specifications.

The dividing wall column and the internals present are chosen in order to obtain the number of theoretical stages necessary in each section. It will be possible to use, as internals, plates, stacked packing, such as structured packing, or random packing.

According to one embodiment, the number of theoretical stages of the prefractionation section S1+S2 is between 1 and 15, and the feed of the column is preferably placed in the final lower third approximately of this section.

According to one embodiment, the number of theoretical stages of the withdrawal section S4+S5 is between 2 and 15, and the point for withdrawal of the purified ester is preferably placed in the final lower quarter approximately of this section.

According to one embodiment, the number of theoretical stages of the rectification section S3 is between 5 and 15.

The column can operate under vacuum, in order to minimize the thermal exposure of the heat-sensitive compounds within the column. Advantageously, the column operates under a vacuum ranging from 10 to 100 mmHg.

Advantageously, the operating temperature is between 50° C. and 160° C.

The internals used for the column can be valve trays or perforated trays having a downcomer, or crosscurrent trays such as dual flow trays, ripple trays, Turbo Grid Shell, or stacked packing such as structured packing such as Mellapack250X from Sulzer.

The process according to the invention has the aim of recovering the (meth)acrylic ester with a purity of greater than 99.6%, preferably greater than 99.8%, starting from a crude reaction mixture obtained according to the known direct esterification processes, in particular according to the processes described in documents EP 609 127 and EP 1 247 793.

The conditions of the esterification reaction are those known to a person skilled in the art and can be implemented according to a process of continuous, semicontinuous or batch type, preferably according to a continuous process.

The esterification catalyst generally used is a homogeneous catalyst, most frequently a homogeneous acid catalyst, such as an organic sulfonic acid, such as methanesulfonic acid, para-toluenesulfonic acid, benzenesulfonic acid, dodecylsulfonic acid, xylenesulfonic acid, or mixtures thereof, or sulfuric acid. Preferably, sulfuric acid is used.

The reaction mixture comprises the ester sought, the residual reactants alcohol and acid—(light compounds), and sulfuric acid in the form of alkyl hydrogen sulfate in the case of sulfuric acid catalysis, and also heavy compounds formed in side reactions.

The heavy compounds originate from Michael addition reactions (Michael adducts). In the case of the synthesis of 2-ethylhexyl acrylate, this concerns in particular 2-ethylhexyl 2ethylhexylpropionate (OOP), 2-ethylhexyl beta-hydroxypropionate or 2-ethylhexyl propoxypropionate, and other products with a high boiling point.

The crude reaction mixture formed in the esterification reactor can be treated directly according to the process of the invention.

According to a preferred alternative, the reaction mixture can be subjected to a neutralization, for example by addition of an aqueous solution of a base such as sodium hydroxide, followed by a decantation, separating an aqueous phase and an organic phase. The aqueous phase makes it possible to separate the salts formed after the neutralization step. The organic phase, after optional washing with water in an extraction column to remove traces of salts, is then sent to the purification system according to the invention.

Under these conditions, the organic phase may have a residual acidity capable of catalyzing the degradation of the Michael adducts during the purification process.

The configuration of the dividing wall column employed in the process according to the invention then makes it possible to avoid the risk of contamination of the product withdrawn as a sidestream.

Apart from the operating conditions suitable for the esterification reaction minimizing the formation of the heavy compounds and optimizing the yield of the reaction, it is necessary to introduce polymerization inhibitors (also known as stabilizers) not only during the reaction but also during the purification of the crude reaction mixture exiting from the esterification reactor.

Mention may be made, as polymerization inhibitors which can be used, for example, of phenothiazine (PTZ), hydroquinone (HQ), hydroquinone monomethyl ether (HQME), di(tert-butyl)-para-cresol (BHT), para-phenylenediamine, TEMPO (2,2,6,6-tetramethyl-1-piperidinyloxy), di(tert-butyl)catechol, or TEMPO derivatives, such as OH-TEMPO, alone or their mixtures in all proportions.

Advantageously, from 100 to 5000 ppm of polymerization inhibitor are introduced during the purification of the reaction mixture into the purification system according to the process of the invention.

To make the inhibitors more efficient, it is advisable to inject oxygen air or air depleted to 7% $O_2$ at the bottom of the column. Preferably, the amount of oxygen injected corresponds to a content of 0.2% to 0.5% relative to the amount of organic vapor in the column.

According to a first embodiment, the purification system is stabilized using a single polymerization inhibitor; preferably injected at the top condenser, the purified (meth)acrylic ester being withdrawn as a sidestream from the dividing wall column in the form of a stabilized liquid or gas stream.

According to this embodiment, it is preferable to use hydroquinone monomethyl ether as stabilizer.

According to a second embodiment, a first polymerization inhibitor, injected at the top condenser, is used to limit the polymerization side reactions in the dividing wall column, and the purified (meth)acrylic ester is withdrawn as a sidestream in the form of a gas stream which, after condensation, is stabilized with a polymerization inhibitor that is different from previous one injected into the top condenser. According to this embodiment, it is possible to use a first inhibitor which is markedly cheaper and to be freed from its presence in the purified product by carrying out a gas-phase withdrawal, the first polymerization inhibitor remaining in the stream of heavy byproducts separated at the column bottom. Phenothiazine is suitable as first polymerization inhibitor as it also makes it possible to stabilize the organic streams. The purified (meth)acrylic ester withdrawn is then stabilized according to conventional practice, for example using hydroquinone methyl ether.

Purified (meth)acrylic ester is understood to mean a product having a (meth)acrylic ester content of >99.6% by weight, preferably >99.8% by weight. Preferably, the content of heavy impurities is less than 1000 ppm. Preferably, the content of residual alcohol is less than 1000 ppm, in particular less than 500 ppm.

The invention thus provides a process for producing a $C_4$-$C_{12}$ (meth)acrylic ester in a compact plant, the investment and operating cost of which is reduced, and providing a product of high purity with an optimized yield.

The examples below illustrate the present invention without, however, limiting the scope thereof.

Experimental Section

In the examples, the percentages are shown by weight, unless otherwise indicated, and the following abbreviations were used:

2EHA: 2-ethylhexyl acrylate
AA: acrylic acid
PTZ: phenothiazine
HQ: hydroquinone

EXAMPLE 1: DEGRADATION TEST OF A COLUMN BOTTOM PRODUCT

This example demonstrates the back-cracking phenomena which arise at the bottom of a conventional DWC distillation column, that is to say one comprising a separating wall which is not joined at the bottom part of the column and a single reboiler associated with the bottom.

The cracking test was carried out in a 1 liter round-bottomed flask surmounted by a condenser in order to ensure operation under complete reflux at atmospheric pressure.

A mixture having a composition close o the composition expected at the bottom of the distillation column at the boiler B1 was introduced into the flask and subjected to a temperature of 147° C. and 156° C. at P atm over a period of 40 minutes.

Chromatographic monitoring of the composition of the reaction mixture was carried out and the results, expressed as mass percentages, are collated in table 1 below.

This test demonstrates the formation of 2-ethylhexanol resulting from, back-cracking reactions under the operating conditions (temperature, pressure, duration) of a conventional DWC purification column.

EXAMPLE 2: COMPARATIVE

A crude reaction mixture resulting from the synthesis by esterification of acrylic acid with 2-ethylhexanol was subjected to a purification treatment using a dividing wall column such as that described in example 1 of document WO 2018/114429.

Simulation using ASPEN Plus software was carried out fora reaction mixture having the following composition by mass:

2EHA: 95%

2-ethylhexanol (2EHOH): 1.5%

2-ethylhexyl 2-ethylhexylpropionate (OOP): 0.76%

2-ethylhexyl beta-hydroxypropionate (2EHHP): 2.4%

2-ethylhexyl acetate (2EHAC): 0.22%

The pressure at the column top is 25 mmHg, the loss of head of the column was set at 48 mmHg.

The top product flow rate is 5462 kg/h and the bottom product flow rate is 1200 kg/h.

The column comprises 26 theoretical stage total. The bottom temperature is 143° C., the top temperature is 111° C.

A mass concentration profile (stage 1: column top; stage 26: column bottom) for the whole column is thus obtained, as shown in table 2.

TABLE 1

|  | 147° C. | | | 156° C. | | |
| --- | --- | --- | --- | --- | --- | --- |
|  | Time, min | | | | | |
|  | 0 | 20 | 40 | 0 | 20 | 40 |
| 2-ethylhexanol | 0.0390 | 0.066 | 0.0701 | 0.0390 | 0.0797 | 0.1120 |
| 2-ethylhexyl acetate | 0.0511 | 0.0493 | 0.0493 | 0.0511 | 0.0498 | 0.0498 |
| 2-ethyl-4-methylpentyl acrylate | 0.0554 | 0.0555 | 0.0563 | 0.0554 | 0.0550 | 0.0547 |
| C8 acrylate | 0.0063 | 0.0110 | 0.0081 | 0.0063 | 0.0131 | 0.0105 |
| 2-ethylhexyl acrylate 2EHA | 81.59 | 81.88 | 81.89 | 81.59 | 81.76 | 81.79 |
| 2-ethylhexyl butanoate | 0.0351 | 0.0346 | 0.0344 | 0.0351 | 0.0346 | 0.0347 |
| dioctyl ether (3 isomers) | 0.0206 | 0.0203 | 0.0196 | 0.0206 | 0.0206 | 0.0207 |
| di(2-ethylhexyl) ether | 0.0277 | 0.0275 | 0.0275 | 0.0277 | 0.0275 | 0.0276 |
| beta-($H_2O$ + 2EHA) | 0.7885 | 0.8152 | 0.8140 | 0.7885 | 0.8203 | 0.8083 |
| (AA + 2EHA) | 1.78 | 1.62 | 1.61 | 1.78 | 1.62 | 1.63 |
| 2-ethylhexyl 2-ethylhexylpropionate | 11.53 | 11.56 | 11.55 | 11.53 | 11.60 | 11.60 |

TABLE 2

| Stage | 2EHOH | 2EHA | OOP | 2EHHP | 2EHAC |
|---|---|---|---|---|---|
| 1 | 0.02570981 | 0.97129935 | 3.05E−07 | 2.66E−05 | 0.00290101 |
| 2 | 0.01626731 | 0.98123475 | 7.44E−07 | 5.62E−05 | 0.00237266 |
| 3 | 0.0149886 | 0.98264069 | 1.06E−06 | 7.59E−05 | 0.00222324 |
| 4 | 0.01466844 | 0.9830128 | 1.50E−06 | 0.00010205 | 0.0021429 |
| 5 | 0.01460183 | 0.98308381 | 2.12E−06 | 0.00013669 | 0.00210175 |
| 6 | 0.01460157 | 0.98305565 | 3.00E−06 | 0.00018257 | 0.00208229 |
| 7 | 0.01461954 | 0.98298269 | 4.24E−06 | 0.00024325 | 0.00207468 |
| 8 | 0.01464346 | 0.98287787 | 5.99E−06 | 0.00032342 | 0.00207347 |
| 9 | 0.01467011 | 0.98274114 | 8.47E−06 | 0.00042922 | 0.00207567 |
| 10 | 0.01469858 | 0.98256681 | 1.20E−05 | 0.0005687 | 0.00207964 |
| 11 | 0.01472855 | 0.98234526 | 1.69E−05 | 0.00075238 | 0.00208448 |
| 12 | 0.01475995 | 0.98206281 | 2.39E−05 | 0.00099401 | 0.00208969 |
| 13 | 0.0147928 | 0.9817011 | 3.37E−05 | 0.00131154 | 0.00209502 |
| 14 | 0.01501932 | 0.98108292 | 4.73E−05 | 0.00172142 | 0.00206767 |
| 15 | 0.00644444 | 0.98978944 | 5.20E−05 | 0.00188171 | 0.00176416 |
| 16 | 0.0026873 | 0.99360468 | 5.79E−05 | 0.0020833 | 0.0014903 |
| 17 | 0.00110501 | 0.99513948 | 6.58E−05 | 0.00234971 | 0.00125318 |
| 18 | 0.00045124 | 0.99561167 | 7.67E−05 | 0.0027091 | 0.00105147 |
| 19 | 0.00018362 | 0.99552906 | 9.19E−05 | 0.00319797 | 0.00088107 |
| 20 | 7.46E−05 | 0.99507182 | 0.00011313 | 0.00386534 | 0.00073745 |
| 21 | 3.03E−05 | 0.99426733 | 0.00014302 | 0.00477799 | 0.00061644 |
| 22 | 1.23E−05 | 0.99306099 | 0.00018517 | 0.00602721 | 0.00051444 |
| 23 | 5.02E−06 | 0.99133933 | 0.00024472 | 0.00773784 | 0.00042837 |
| 24 | 2.05E−06 | 0.98893046 | 0.00032893 | 0.01008068 | 0.00035567 |
| 25 | 8.35E−07 | 0.98559199 | 0.00044809 | 0.01328907 | 0.00029417 |
| 26 | 4.88E−07 | 0.9831384 | 0.00053576 | 0.01563413 | 0.00026547 |

At plates 18-19-20, the compositions are close to those obtained in example 1 of document WO 2018114429, and the purity of the product 2EHA is of the order of 99.5%.

However, the Aspen simulation does not take account of the back-cracking phenomena that can arise in the column.

To simulate the effect of the back-cracking on the quality of the product that would be obtained at plates 19 and 20, a simulation test was carried out under the same conditions but after having added, at the bottom of the column in the boiler, a stream of 1.2 kg/h 2-ethylhexanol, or 1900 ppm relative to the bottom stream.

A mass concentration profile (stage 1: column top; stage 26: column bottom) the whole column is thus obtained, as shown in table 3.

TABLE 3

| Stage | 2EHOH | 2EHA | OOP | 2EHHP | 2EHAC |
|---|---|---|---|---|---|
| 1 | 0.02599795 | 9.71E−01 | 3.04E−07 | 2.65E−05 | 0.00290011 |
| 2 | 0.01645191 | 9.81E−01 | 7.44E−07 | 5.62E−05 | 0.00237224 |
| 3 | 0.01515807 | 9.82E−01 | 1.05E−06 | 7.59E−05 | 0.00222285 |
| 4 | 0.0148339 | 9.83E−01 | 1.49E−06 | 0.000102 | 0.0021425 |
| 5 | 0.01476637 | 9.83E−01 | 2.12E−06 | 0.00013663 | 0.00210133 |
| 6 | 0.01476604 | 9.83E−01 | 2.99E−06 | 0.00018249 | 0.00208185 |
| 7 | 0.01478418 | 9.83E−01 | 4.24E−06 | 0.00024314 | 0.00207423 |
| 8 | 0.01480835 | 9.83E−01 | 5.99E−06 | 0.00032328 | 0.00207302 |
| 9 | 0.01483529 | 9.83E−01 | 8.47E−06 | 0.00042905 | 0.00207522 |
| 10 | 0.01486406 | 9.82E−01 | 1.20E−05 | 0.00056847 | 0.00207918 |
| 11 | 0.01489436 | 9.82E−01 | 1.69E−05 | 0.00075209 | 0.00208402 |
| 12 | 0.0149261 | 9.82E−01 | 2.39E−05 | 0.00099364 | 0.00208923 |
| 13 | 0.01495931 | 9.82E−01 | 3.37E−05 | 0.00131108 | 0.00209456 |
| 14 | 0.01518837 | 9.81E−01 | 4.72E−05 | 0.00172083 | 0.00206722 |
| 15 | 0.0066295 | 9.90E−01 | 5.19E−05 | 0.00188104 | 0.00176376 |
| 16 | 0.00287779 | 9.93E−01 | 5.79E−05 | 0.00208256 | 0.00148998 |
| 17 | 0.00129682 | 9.95E−01 | 6.58E−05 | 0.00234888 | 0.00125295 |
| 18 | 0.00064303 | 9.95E−01 | 7.67E−05 | 0.00270817 | 0.00105131 |
| 19 | 0.00037506 | 9.95E−01 | 9.19E−05 | 0.0031969 | 0.00088096 |
| 20 | 0.00026564 | 0.9948822 | 0.00011309 | 0.00386409 | 0.00073738 |
| 21 | 0.000221 | 0.99407828 | 0.00014297 | 0.0047765 | 0.0006164 |
| 22 | 0.00020275 | 0.99287252 | 0.00018511 | 0.00602538 | 0.00051442 |
| 23 | 0.0001953 | 0.99115146 | 0.00024464 | 0.00773558 | 0.00042837 |
| 24 | 0.00019229 | 0.98874325 | 0.00032882 | 0.01007783 | 0.00035568 |
| 25 | 0.0001912 | 0.98540548 | 0.00044796 | 0.01328544 | 0.00029419 |
| 26 | 0.00027885 | 0.98286735 | 0.00053549 | 0.0156273 | 0.00026546 |

At plates 18-19-20, the quality of the pure product 2EHA is altered, confirming the negative impact of generation of 2-ethylhexanol on a product with sidestream withdrawal placed 6-8 theoretical plates above the boiler. Under these conditions, the purity of the 2EHA withdrawn at plate 20 is less than 99.5%.

EXAMPLE 3: ACCORDING TO THE INVENTION

A simulation was carried out using the ASPEN Plus software for a purification system as shown in the appended FIGURE.

The feed is identical to that of example 2, with addition at the boiler of the prefractionation section of 1000 ppm of 2-ethylhexanol in order to simulate cracking.

The number of plates of the different sections is as follows:

N1: 12—N2: 2—N3: 12—N4: 8—N5: 6

In this configuration, 2EHA with a purity of greater than 99.7% was obtained with a residual 2-ethylhexanol content of 50 ppm.

According to the invention, a separating wall extending as far as the bottom of the column makes k possible to prevent the back-cracking products such as 2-ethylhexanol from contaminating the product withdrawn as a sidestream.

This example confirms the importance of the positioning of the separating wall in the dividing wall column for the quality of the product obtained in sidestream withdrawal, in particular the need to have a wall separating the bottom part of the column.

EXAMPLE 4: 2-OCTYL ACRYLATE TAILING

This test was carried out using a pilot column of ND 200 mm to characterize the back-cracking phenomena which can also arise in a process for manufacturing 2-octyl acrylate starting from 2-octanol and acrylic acid.

The main impurities present in the feed of the column, in the bottom of the column and in the top of the column are presented in table 4 below.

TABLE 4

| Mass balance, % | Feed | Column bottom | Column top | O/I balance (%) |
|---|---|---|---|---|
| Mass flow rate (kg/h) | 65 | 24 | 41 | |
| Acrylic acid | 0.0075 | 0.0265 | 0.025 | 241 |
| 2-Octyl acrylate | 99.6965 | 99.2427 | 99.7135 | 0 |
| 2-Octanol | 0.0687 | 0.182 | 0.1323 | 119 |
| Octenes | 0.0389 | 0.1625 | 0.1267 | 260 |
| AA + alcohol | 0.1865 | 0.3856 | | −24 |
| Phenol | 0.0001 | 0.0001 | 0.0002 | 63 |
| 2-Octyl acetate | 0.0018 | 0.0006 | 0.0023 | −7 |

The balance between the output and the input O/I makes it possible to verify the variation in the species present in the streams.

During this distillation, a great increase in the content of acrylic acid, 2-octanol and octenes is observed, which indicates that the reaction mixture undergoes cracking reactions under the distillation conditions.

The invention claimed is:

1. A process for recovering a purified $C_4$-$C_{12}$ (meth) acrylic ester, starting from a crude reaction mixture including Michael adducts obtained by direct esterification of the (meth)acrylic acid with the corresponding $C_4$-$C_{12}$ alcohol wherein said process comprises the step of:
using a purification system comprising a dividing wall column equipped with a separating wall which is not joined to the upper dome of the column in the top part and is joined to the bottom of the column in the bottom part, and associated at the top with a single condenser and at the bottom with two boilers, said dividing wall column comprising a common rectification section above the wall, a prefractionation section comprising a feed of the crude reaction mixture of the column, and a withdrawal section separated from the prefractionation section by the wall and comprising the withdrawal of the purified ester; wherein said dividing wall column further comprises an outlet at the upper dome of the column, two outlets at the bottom part of the column and one outlet at the withdrawal section.

2. The process as claimed in claim 1, wherein a gas stream is extracted at the top of the rectification section and recycled after condensation at least in part into an esterification reactor.

3. The process as claimed in claim 1 wherein a stream is withdrawn at the bottom of the prefractionation section and recycled at least in part into an esterification reactor.

4. The process as claimed in claim 1 wherein a stream is withdrawn at the bottom of the withdrawal section and recycled at least in part into the prefractionation section of the dividing wall column.

5. The process as claimed in claim 1 wherein a stream of purified (meth)acrylic ester is withdrawn as a sidestream from the withdrawal section at a point situated above the bottom withdrawal of said withdrawal section.

6. The process as claimed in claim 1 wherein the purification system is stabilized using a single polymerization inhibitor, the purified (meth)acrylic ester being withdrawn as a sidestream from the dividing wall column in the form of an already stabilized liquid or gas stream.

7. The process as claimed in claim 1 wherein the purification system is stabilized using a first polymerization inhibitor, the purified (meth)acrylic ester being withdrawn as a sidestream from the dividing wall column in the form of a gas stream which, after condensation, is subsequently stabilized with a polymerization inhibitor that is different from the first inhibitor.

8. The process as claimed in claim 1 wherein the number of theoretical stages of the prefractionation section is between 1 and 15.

9. The process as claimed in claim 1 wherein the number of theoretical stages of the withdrawal section is between 2 and 15.

10. The process as claimed in claim 1 wherein the number of theoretical stages of the rectification section is between 5 and 15.

11. The process as claimed in claim 1 wherein the (meth)acrylic ester is 2-ethylhexyl acrylate or 2-octyl acrylate.

12. A process for producing a $C_4$-$C_{12}$ (meth)acrylic ester of high purity by direct esterification of the (meth)acrylic acid with the corresponding $C_4$-$C_{12}$ alcohol, wherein the crude reaction mixture is subjected to the recovery process using the purification system as claimed in claim 1.

13. The process as claimed in claim 1 where the prefractionation section and the withdrawal section further comprise liquid reflux provided by a collecting means thereby allowing controlled distribution of liquid from a bottom of the rectification section to the prefractionation and withdrawal sections.

\* \* \* \* \*